United States Patent [19]

Kauvar et al.

[11] Patent Number: 5,767,086
[45] Date of Patent: Jun. 16, 1998

[54] BONE MARROW STIMULATION BY CERTAIN GLUTATHIONE ANALOGS

[75] Inventors: Lawrence M. Kauvar, San Francisco; Matthew H. Lyttle, Point Reyes Station; Amy S. Morgan, Oakland, all of Calif.; Richard F. Borch, Pittsford, N.Y.

[73] Assignee: Terrapin Technologies, Inc., South San Francisco, Calif.

[21] Appl. No.: 482,645

[22] Filed: Jun. 7, 1995

Related U.S. Application Data

[63] Continuation-in-part of Ser. No. 305,993, Sep. 19, 1994, abandoned, which is a continuation-in-part of Ser. No. 126,229, Sep. 24, 1993, Pat. No. 5,599,903, which is a continuation-in-part of Ser. No. 863,564, filed as PCT/US94/10797 Sep. 23, 1994, abandoned.

[51] Int. Cl.[6] .............................. A61K 38/06; C07K 5/08
[52] U.S. Cl. .............................................. 514/18; 530/331
[58] Field of Search ................................ 514/18; 530/331

[56] References Cited

U.S. PATENT DOCUMENTS 4,851,388  7/1989  Bright .
5,204,241  4/1993  Pero .
5,430,045  7/1995  Goldberg et al. .

*Primary Examiner*—Paula K. Hutzell
*Assistant Examiner*—Benet Prickril
*Attorney, Agent, or Firm*—Morrison & Foerster LLP

[57] ABSTRACT

Compounds of the formula $$YCO-NHCHCO-G^* \atop | \atop CH_2-Z-X \qquad (1)$$

and the esters, amides, amide/esters and salts thereof, wherein YCO is γ-glu or β-asp;

G* is phenyl glycine or glycine;

Z is $CH_2$, O or S; and

X is a hydrocarbon radical of 1–20 C;

are useful in stimulating the differentiation of bone marrow, mitigating the bone-marrow-destructive effects of a chemotherapeutic agent, and in potentiating the toxicity of chemotherapeutic agents.

12 Claims, 7 Drawing Sheets

BONE MARROW STIMULATION BY CERTAIN GLUTATHIONE ANALOGS

This application is a continuation-in-part of U.S. application Ser. No. 08/305,993 filed 19 Sep., 1994, now abandon, which is a continuation-in-part of 08/126,229 filed 24 Sep., 1993, now U.S. Pat. No. 5,599,903 which is a continuation-in-part of 07/863,564 filed 3 Apr., 1992, now abandoned. This application claims priority from PCT/US94/10797 filed 23 Sep., 1994. The contents of these applications are incorporated herein by reference.

TECHNICAL FIELD

The invention relates to the metabolic effects of a class of glutathione analogs interactive with at least one glutathione S-transferase class. More particularly, the invention is directed to stimulation of bone marrow by this class of glutathione S-transferase inhibitors.

BACKGROUND ART

PCT application W095/08563 published 30 Mar., 1995, and based on PCT/US94/10797, from which the present application claims priority, discloses tripeptide compounds which are analogs of glutathione. These tripeptide compounds generally are inhibitors of glutathione S-transferase activity and the various compounds contained in this group show diverse specificities with respect to glutathione S-transferase enzymes.

A subset of these analogs, which are of the general formula and the amides and esters thereof, wherein YCO is γ-glu or β-asp; G* is phenyl glycine or glycine; Z is $CH_2$, O or S; and X is a hydrocarbon radical of 1–20 C, have now been found to have the ability to stimulate the metabolism of bone marrow and therefore exert protective effects when chemotherapeutic agents destructive to the bone marrow are administered. This same subset of glutathione analogs shows inhibition of the π class of glutathione S-transferase (GST), and, in some cases, other classes as well.

DISCLOSURE OF THE INVENTION

The invention provides compounds which are useful in inducing bone marrow stimulation generally and as aids to chemotherapeutic treatment of tumors by virtue of their ability to exert a protective effect on the bone marrow with respect to toxic agents which are otherwise useful in chemotherapy.

Thus, in one aspect, the invention is directed to a method to stimulate the differentiation of bone marrow progenitor cells which method comprises contacting said bone marrow with a compound of the formula or the ester, amide, ester/amide or salt forms thereof,
wherein YCO is γ-glu or β-asp;
G* is phenyl glycine or glycine;
Z is $CH_2$, O or S; and
X is a hydrocarbon radical of 1–20 C;
in an amount and for a time effective to stimulate the differentiation of said bone marrow.

In another aspect, the invention is directed to a method to mitigate the bone marrow-destructive effects of a chemotherapeutic agent administered to a subject, which method comprises administering the compound of formula (1) to said subject in an amount and for a time effective to exert said protective effects.

In still another aspect, the invention is directed to a method to stimulate the differentiation of bone marrow or to protect the bone marrow against chemotherapeutic effects which method comprises contacting said bone marrow with a compound which inhibits glutathione S-transferase isoenzymes of at least one class, and generally inhibits GST of the π class at a reasonable level.

MODES OF CARRY OUT THE INVENTION

The compounds useful in the methods of the invention have the common properties of the ability to inhibit the activity of at least one isoenzyme subclass of the glutathione S-transferase isoenzymes and to stimulate the differentiation of bone marrow, even in the presence of agents which ordinarily would destroy such differentiation. These compounds are of the formula wherein YCO, G*, Z and X are defined as above. When used in vivo, or in vitro for the purpose of affecting intact cells, the compounds of the invention are preferably in the amide, ester or hybrid amide/ester forms.

It will be apparent that the compounds of the invention may be present as the free acids, salts, monoesters, diesters, monoamides, diamides or hybrid ester/amide forms. The amides and esters useful in the invention are generally those of alkyl (1–10 C); alkenyl (1–10 C); and arylalkyl (7–12 C) alcohols and amines Thus, typical esters and amides useful in the invention include dimethyl esters, diethyl esters, mixed ethyl/propyl esters, dihexyl esters, mixed hexyl/octyl esters, dibutenyl esters, mixed butenyl/vinyl esters, the corresponding amides, and the like. Especially preferred are the diethyl ester forms of the compounds of formula (1). A preferred embodiment of Z is O or S, particularly S; and a preferred embodiment of YCO is γ-glu.

Preferred embodiments for the hydrocarbon (1-20 C) moiety of X include hexyl, heptyl, octyl, benzyl and naphthyl. Particularly preferred compounds of the invention are γE-C(octyl)-φG; γE-C(Hx)-φG; γE-C(naphthyl)-φG; γE-C(Bz)-φG; and γE-C(octyl)-G; γE-C(Hx)-G; and γE-C(Bz)-G; and especially their diethyl esters. Particularly preferred are γE-C(Bz)-φG diethyl ester (TER199) and γE-C(octyl)-G (TER183).

The compounds of the invention have several properties which make them useful as adjuncts to chemotherapy. First, they stimulate the differentiation of bone marrow, the destruction of which is a common side-effect of chemotherapeutic agents. Second, they inhibit at least one class of the GST isoenzymes, including the π subclass, which is particularly prevalent in tumor cells. Third, the compounds of formula (1) directly potentiate the effect of chemotherapeutic agents in the destruction of tumor cells. This combination of qualities makes the compounds of the invention useful both as bone marrow potentiating agents directly and to ameliorate the negative effects of chemotherapeutic protocols, as well as enhancing the toxic effect to the target cells. When formulated for use in vivo or in contact with intact cells, the compounds of formula (1) will preferably be supplied as the esters, preferably the diesters, more preferably the diesters of saturated alcohols containing 1-5 C, more preferably 1-3 C, and most preferably as the diethyl esters.

By "stimulating the differentiation of bone marrow, including the differentiation of bone marrow progenitor cells" is meant enhancing the properties of bone marrow in the direction of exhibiting an increased capacity to form colonies of differentiated cells, in particular, granulocyte macrophage. It is unclear what the mechanism of this stimulation is; the cells themselves may or may not be directly stimulated by the compounds of the invention; rather, the increase in colonies of differentiated cells may be due to preferential survival, inhibition of apoptosis, or any one of a number of factors. As used in the present application, "stimulating the differentiation of bone marrow" refers to the enhanced ability of bone marrow to exhibit colony formation at a higher level than unstimulated bone marrow.

The formulations will employ standard methods such as those described in *Remington's Pharmaceutical Sciences*, latest edition, Mack Publishing Company, Easton, Pa. The compounds may be formulated for injection, for oral administration, or for alternative methods of administration such as transmucosal or transdermal administration. Injection can be intravenous, intraperitoneal, intramuscular, or by any other conventional route. As shown hereinbelow, the compounds of the invention are effective when administered orally as well as when introduced directly into the blood stream.

Suitable subjects who will benefit from administering the compounds of the invention include vertebrate subjects, particularly mammalian or human subjects whose bone marrow progenitor cells inadequately differentiate. Failure to bone marrow cells to differentiate occurs, in particular, when the subject has been exposed to bone marrow destructive agents, such as chemotherapeutic agents, radiation, exposure to toxins in the environment and the like. Also included are those with bone marrow degenerative diseases and conditions.

The dosage required depends on the nature of the subject, the nature of the condition, the manner of administration, and the judgment of the attending physician or veterinarian. Suitable dosage ranges are adjusted according to these parameters.

The following examples are intended to illustrate, but not to limit, the invention.

EXAMPLE 1

Use of the Compounds of the Invention in Potentiation of Cytotoxic Agents in Human Cells This example describes: 1) potentiation in human tumor cells of a cytotoxic agent currently used in cancer chemotherapy by GST inhibitors, including compounds of the present invention, as well as 2) enhanced intracellular efficacy of esterified forms of these compounds.

HT-29 (human colon adenocarcinoma) cells were obtained from Dr. Roberto Ceriani (Cancer Research Fund of Contra Costa County, Walnut Creek, Calif.) and were used in log phase of growth unless otherwise specified. Chlorambucil (CMB) was obtained from Sigma (St. Louis, Mo.) and was dissolved in 100% ethanol. All GST inhibitors were dissolved in ethanol, DMSO, or water just prior to use. The same amount of solvent added to culture medium served as the vehicle control.

In a modified clonogenic assay for cytotoxicity, cells were suspended at $2 \times 10^5$ cells/ml in serum-free medium in the presence of vehicle or inhibitor. Inhibitors were used at concentrations that resulted in $\geq 90\%$ survival in the presence of inhibitor alone, when compared to vehicle treated cells. Cells were incubated for 2 hours, then varying doses of CMB were added. At the end of a second 2-hour incubation, cells were diluted to $7.5-10\times 10^3$/ml in serum-containing medium and plated in quadruplicate at 200 μl/well in Microtest III microtiter plates.

Plates were incubated for 6 days and assayed by a modified methylene blue method. Briefly, cells were fixed with 1.25% glutaraldehyde in PBS then stained with 0.05% methylene blue in distilled water. Plates were washed several times in distilled water to remove unretained dye and retained dye was resolubilized in 0.03N HCl. Plates were read at 650 nm in a Molecular Devices Vmax plate reader (Molecular Devices, Redwood City, Calif.). $IC_{50}$ values (inhibitor concentration causing 50% reduction in cell viability) were determined for the drug in the presence or absence of inhibitor from dose-response curves. A dose modification factor (DMF), a measure of potentiation of cytotoxicity, was calculated for each inhibitor by dividing the $IC_{50}$ value of CMB without inhibitor treatment by the $IC_{50}$ value for CMB with inhibitor treatment.

Results of potentiation tests with several GST inhibitors in HT29 cell cultures are summarized in Table 1.

TABLE 1

Potentiation of Chlorambucil Cytotoxicity in Human Cells by GST Inhibitors and Their Esters

| | Parent Compound | | Diethyl ester | |
|---|---|---|---|---|
| GST Inhibitor | Dose tested[a] (μM) | DMF[b] | Dose tested[b] (μM) | DMF[b] |
| γE-C(octyl)-G | N.D. | — | 5 | 0.86 ± 0.02 |
| γE-C(Hx)-φG | 100 | 1.1 ± 0.02 | 12.5 | 1.27 ± 0.02 |
| γE-C(Bz)-φG | 100 | 1.08 ± 0.01 | 12.5 | 1.65 ± 0.04 |

TABLE 1-continued

Potentiation of Chlorambucil Cytotoxicity in Human Cells by GST Inhibitors and Their Esters

| | Parent Compound | | Diethyl ester | |
|---|---|---|---|---|
| GST Inhibitor | Dose tested[a] (μM) | DMF[b] | Dose tested[b] (μM) | DMF[b] |
| γE-C(naphthyl)-G | 200 | | 12.5 | 1.21 ± 0.01 |

[a]Test dose was determined from toxicity curve and analogs were used at the dose at which ≧90% survival occurred in the presence of the analog alone.
[b]Dose modification factor. Values are mean ± S.D. of 2–3 experiments.

The results in Tables 1–3 show that several GSH analogs found to be inhibitors of GSH also potentiate killing of human tumor cells in culture by CMB which is a substrate for various GSTs. Further, as shown in Table 1, this potentiation is greatly enhanced by esterification which is designed to enhance uptake of the GST inhibitors. Thus, γE-C(Bz)-φG at 100 μM did not enhance cell killing by CMB, reducing the concentration CMB needed for 50% cell killing by a DMF of 1.08. In contrast the diethyl ester of γE-C(Bz)-φG at only 12.5 μM enhanced CMB cytotoxicity by a factor of 1.65.

Preferential expression of GST isoenzyme P1-1 has been reported in a range of human tumors. In the present study the efficacy of CMB potentiation of the several GST inhibitors tested correlated directly with their potencies as inhibitors of the human π-class GST

TABLE 2

Rank Correlation of Chlorambucil Dose Modification Factors (DMFs) of GST Inhibitors with $K_i$ value for Inhibition of Human GST P1-1

| Rank Inhibitor order | Relative Ki value of parent compound | Rank order | DMF[a] of DEE |
|---|---|---|---|
| γE-C(Bz)-φG | 1 | 1 | 1.651 |
| γE-C(Hx)-φG | 2.1 | 2 | 1.272 |
| γE-C(naphthyl)-G | 3 | 3 | 1.213 |
| γE-C(octyl)-G | 4.8 | 4 | .864 |

[a]Dose modification factor of diethyl ester. Values are mean ± S.D. of 2–3 experiments.

The effect of esterification or amidation of the compounds of Formula (1) on their potentiation of chlorambucil cytotoxicity in HT-29 cells was also determined. The DMF was determined for the diethyl ester, the diamide, and the ester/amide of γE-C(Bz)-φG at relevant concentrations. The diester showed a DMF of 1.65+ 0.04 for chlorambucil toxicity at 12.5 μM; the diamide showed a DMF of 1.0 in a single experiment at 200 μM; the ester/amide hybrid showed a DMF of 1.45±0.16 at 50 μM concentration. The results for the diethyl ester and the ester/amide hybrid are given as the mean ±SD of three experiments.

Octyl G (TER183) and Benzyl PG (TER199) were tested in a standard clonogenic assay using three cell lines: HT4-1, a subclone of HT-29; SKOV-3 an ovarian carcinoma, and VLB, a vinblastine-resistant variant of SKOV-3. Three chemotherapeutic drugs, chlorambucil, adriamycin and mitomycin C were used as the toxic agents. In these assays, the cells were seeded at 300 cells/well in 2 ml of medium in 6-well plates in the presence of the compounds of the invention as the diethyl esters. The compounds were used at concentrations that resulted in more than 85% survival when compared to controls. After incubation for 1–2 hours to permit cells to attach, varying doses of the chemotherapeutic agents were added. At least three replicate wells were plated for each test condition and the plates were incubated for two weeks. Colonies were fixed in 95% ethanol and stained with crystal violet for colony counting. $IC_{50}$ values were determined for the chemotherapeutic agent in the presence or absence of the compound of the invention and dose modification factors were calculated by dividing the $IC_{50}$ value of drug without the invention compound by the $IC_{50}$ value of the drug with the invention compound. The modification factors obtained in each protocol are shown in Table 3.

TABLE 3

Ability of selected GSH analogs to potentiate drug toxicity as demonstrated in a clonogenic assay

| Cell Line | GSH Analog | DMF[a] for: | | |
|---|---|---|---|---|
| | | Chlorambucil | Adriamycin | Mitomycin C |
| HT4-1 | Diethyl ester of benzyl PG (25 μM) | 3.28 | 1.2 | n.d.[b] |
| | Diethyl ester of octyl G (5 μM) | 1.74 | 1.13 | 1.56 |
| SKOV-3 | Diethyl ester of benzyl PG (25 μM) | 1.24 | 1.14 | 1.03 |
| | Diethyl ester of octyl G (2.5 μM) | 1.03 | 1.24 (@5 uM)[c] | n.d.[b] |
| VLB | Diethyl ester of benzyl PG (25 μM) | N.D.[d] | 2.5 | .82 (@5 uM)[c] |
| | Diethyl ester of octyl G (5 μM) | N.D.[d] | 1.06 | 1.63 |

[a]Dose modification factor.
[b]No data due to toxicity of analog.
[c]Test dose was different from listed at the left.
[d]Not determined.

As shown in the table, significant modification was obtained when chlorambucil was used as the drug versus HT4-1 cells in the presence of 25 μM of the diethyl ester of benzyl PG. Significant modification was also achieved in VLB cells when treated with adriamycin in the presence of 25 μM of the same compound.

Figure 1A:
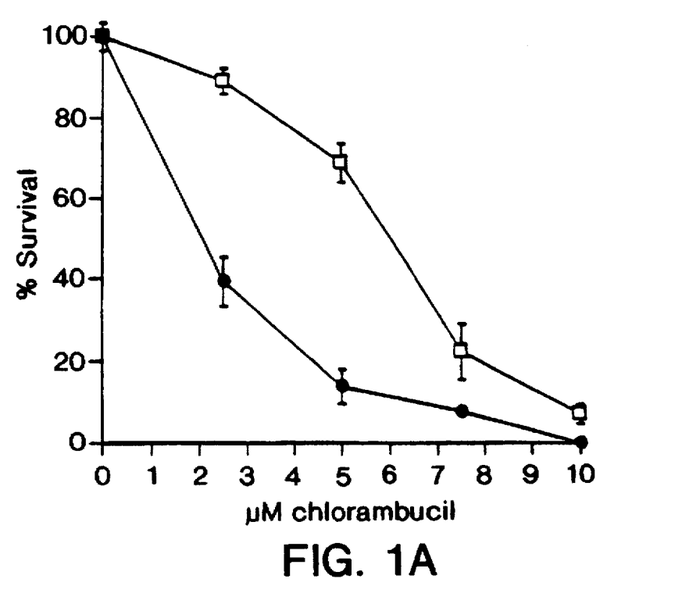
FIG. 1a shows the effect of TER199 on the survival of tumor cells treated with various concentrations of chlorambucil.
Figure 1B:
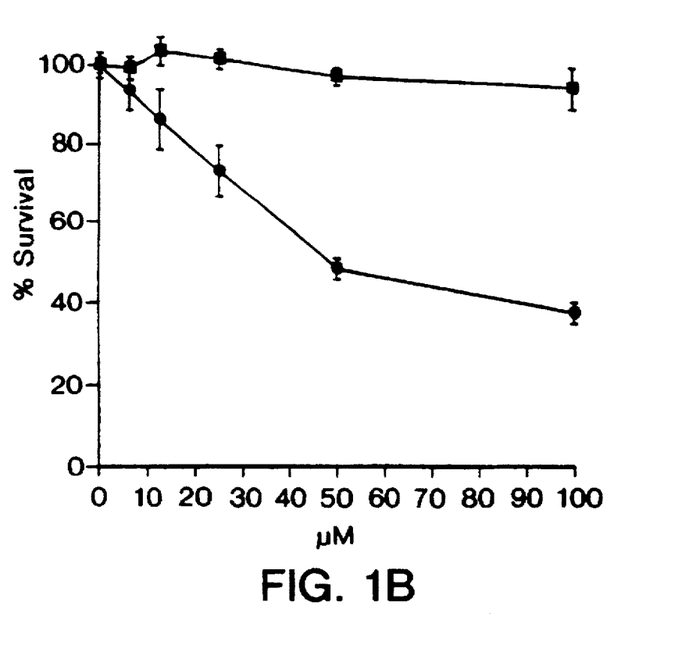
FIG. 1b shows the toxic effect of TER199 in contrast to its unesterified form on HT4-1 cells.

FIG. 1a illustrates the results for varying dosages of chlorambucil and the modifying effect of 25 μM of the diethyl ester of benzyl PG. The open squares (□) represent chlorambucil alone, the closed circles (●) chlorambucil in the presence of the invention compound. As seen in FIG. 1a, the survival rate is markedly diminished when the invention compound is added. FIG. 1b confirms that the diethyl ester is necessary to penetrate the cells. HT4-1 cells were tested for survival in the presence of either benzyl PG (closed squares, ■) or its diethyl ester (closed circles, ●). Unesterified diethyl G has substantially no effect on these cells while the diethyl ester is clearly toxic.

EXAMPLE 2

Metabolic Effects of the Invention Compounds

The metabolic effects related to toxicity of the compounds of the invention on HT-29 cells, were tested using a Cytosensor Microphysiometer made by Molecular Devices, Inc., Menlo Park, Calif. and described in McConnell, H. M. et al. *Science* (1992) 257:1906–1912 and by Wada, H. G. et al. *AATEX* (1992) 1:154–164. Changes in pH of the culture medium are measured as a function of cellular metabolism. Acidification rates of the small volume of liquid flowing over the cells correlate with the number of live cells in the reaction chamber; a reduction of acidification rate reflects reduced numbers of surviving cells.

In this illustration, HT-29 cells were plated at $4 \times 10^5$ cells/chamber in a medium containing 10% fetal calf serum. After 16–18 hours the serum level was reduced to 1% and the cells were maintained for another 18 hours. Cells were then exposed to either ethacrynic acid (50 µM), the diethyl ester of benzyl PG (20 µM) or a vehicle (0.1% ethanol) for 4 hours. The medium was then replaced with serum-free low buffer capacity medium and Microphysiometer analysis was initiated. Half of the chambers were exposed to 100 µM chlorambucil and the other half to vehicle (0.1% ethanol). Acidification rates were monitored for 16 hours and the data are expressed as percentage of the basal (100%) acidification rates.

Figure 2:
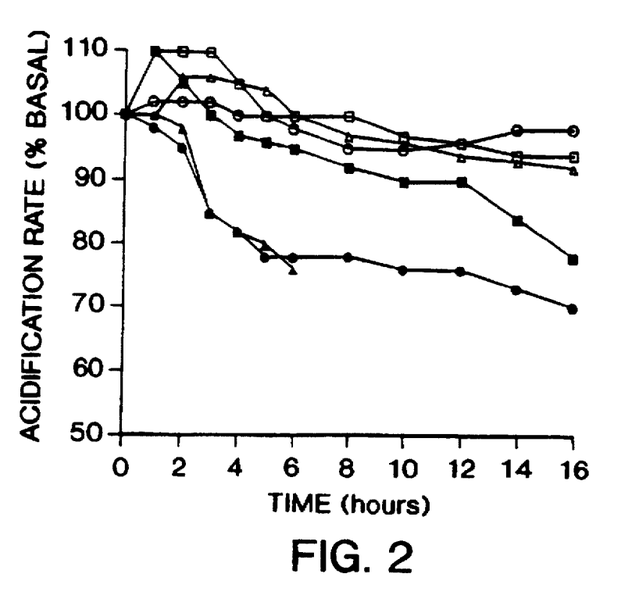
FIG. 2 is a graph showing the effect of various combinations of chlorambucil either alone or in combination with ethacrynic acid or TER199.

The results are shown in FIG. 2. Neither the diethyl ester of phenyl PG nor ethacrynic acid alone had any appreciable effect on acidification rates; however, both ethacrynic acid pretreatment and pretreatment with the benzyl PG diethyl ester potentiated the effect of chlorambucil. In the figure, the open symbols reflect no addition of chlorambucil; the closed symbols reflect addition of chlorambucil; the squares reflect the pretreatment with vehicle, triangles pretreatment with ethacrynic acid, and circles pretreatment with benzyl PG diethyl ester.

EXAMPLE 3

Stimulation of Bone Marrow Granulocyte Macrophage (GM) Progenitors

Figure 3:
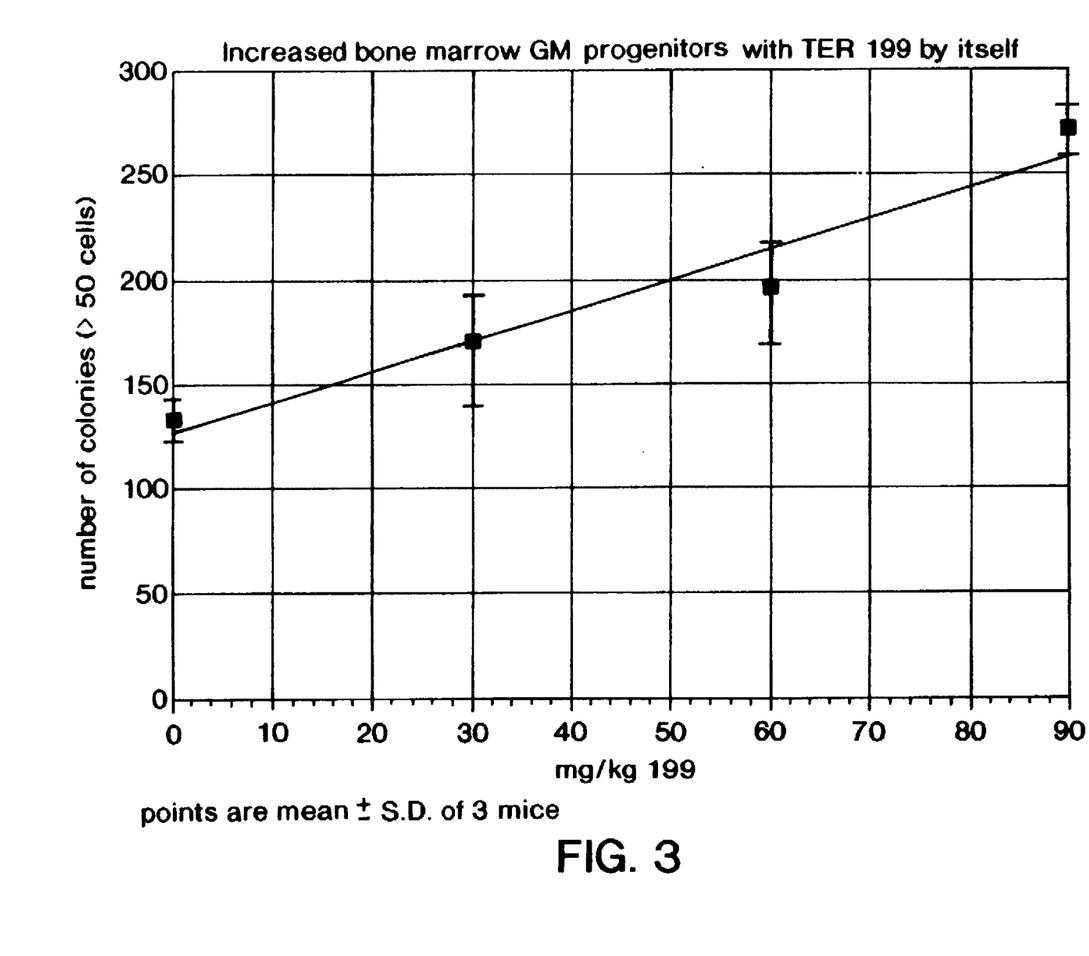
FIG. 3 shows the stimulation of bone marrow granulocyte macrophage progenitors in the presence of TER199.

The compounds of the invention, when esterified so as to be able to penetrate cells, also stimulate the production of GM progenitors in bone marrow when administered to mammalian subjects. In an illustrative assay, three B6D2F$_1$ mice were treated with various doses of benzyl PG intraperitoneally. Femoral bone marrows were harvested 24 hours later and assayed for GM-CFC by the method of East, C. J. et al. *Cancer Chemother Pharmacol* (1992) 31:123–126. An increase in the number of colonies in a dose-dependent manner up to a dosage of 90 mg/kg of benzyl PG was obtained. These results are shown in FIG. 3. At 90 mg/kg, approximately 275 colonies/$10^4$ nucleated cells were obtained compared to about 140/$10^4$ nucleated cells colonies for controls.

EXAMPLE 4

Potentiation of Melphalan Toxicity in vivo

Male scid mice were subcutaneously implanted with HT4-1 tumors from donor mice. When tumors reached approximately 100 mm$^3$, the mice were randomized into six treatment groups and treated for seven days as follows:

1. 5 mg/kg melphalan;
2. 10 mg/kg ethacrynic acid;
3. 60 mg/kg diethyl ester of benzyl-PG;
4. 5 mg/kg melphalan+10 mg/kg ethacrynic acid;
5. 5 mg/kg melphalan+60 mg/kg diethyl ester of benzyl-PG;
6 vehicle alone.

The mice were monitored for weight changes and tumor volumes were determined by measurement with calipers. The tumor growth was monitored until the average tumor size reached 1500 mm$^3$ for all groups except melphalan with ethacrynic acid. This group failed to reach this volume even after 72 days.

The results were computed in terms of the tumor volume in the drug treated mice as a percentage of control tumor volume (i.e., in the group administered vehicle alone). In group 1, administered melphalan alone, the tumors were approximately 75%, of the volume of controls. In group 5 when the diethyl ester of benzyl-PG was administered along with the melphalan, the tumor volume mean was approximately 55% of control. For group 4 administered a combination of melphalan and ethacrynic acid, the volumes were approximately 35% of control. Thus, both ethacrynic acid and diethyl ester of benzyl-PG potentiate the effects of melphalan. (The volume measurements were taken at the time control tumors reached 1500 mm$^3$.)

EXAMPLE 5

Comparison of Intraperitoneal and Oral Administration

Male B6D2F$_1$ mice, five weeks old, 20–24 grams were divided into groups of three mice and administered various dosages of TER199 (diethyl ester of γ-glu-C(Bz)-φG) either orally or intraperitoneally. The TER199 was prepared in sterile nanopore water and administered orally using a gavage tube and a 1 cc syringe or intraperitoneally in saline using a 1 cc syringe with a 28 gauge needle. Mice in the control group were injected with water or saline. Bone marrow cells were harvested 24 hours after drug treatment and added to alpha minimum essential medium (alpha MEM) supplemented with methylcellulose (0.8% w/v), fetal bovine serum (20% v/v), deionized BSA (1% w/v), Pokeweed mitogen-stimulated spleen-cell conditioned medium (PWM-SCCM)[1] (10% v/v) and gentamycin (50 µg/ml). One ml aliquots were plated (four replicate plates) and incubated for seven days at 37° C. A dissecting microscope was used to count the granulocyte/macrophage colonies having more than 50 cells per colony (GM-CFC).

[1]Pokeweed mitogen-stimulated spleen cell condition medium (PWM-SCCM) was prepared according to the procedure of Gringeri et al., 1988. Spleens were removed aseptically from four male B6D2F$_1$ mice enforced through a 200 µm wire mesh screen to obtain a single cell suspension. Ten ml of the suspension (2–4×10$^7$ cell/ml was added to 90 ml alpha-MEM supplemented with 1% deionized BSA, 50 µg/ml gentamicin, 0.3% freshly reconstituted pokeweed antigen, 10 µM 2-mercaptoethanol. The mixture was incubated for 5 days at 37° C. in a 5% CO$_2$ atmosphere and the resulting conditioned medium was centrifuged at 800 g for ten minutes and filtered through a 0.22 µm filter. Aliquots were kept frozen at −20° C. until use.

Figure 4:
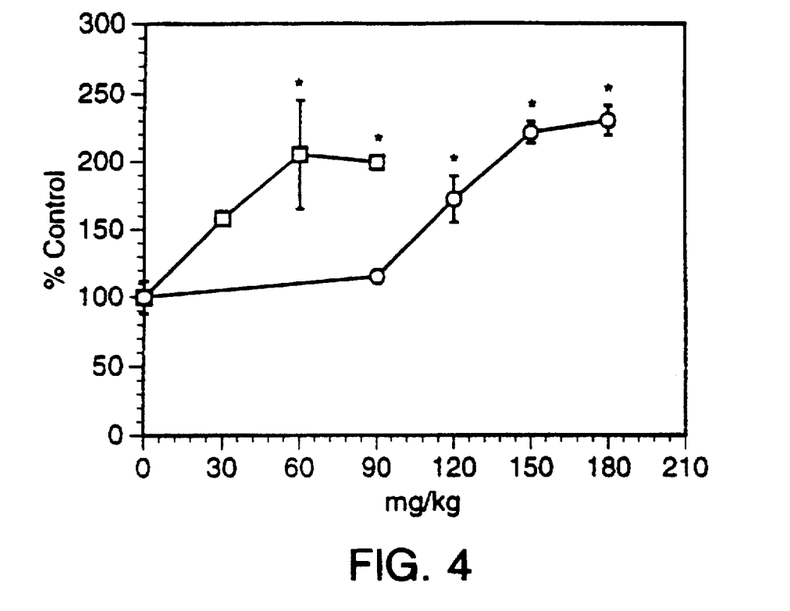
FIG. 4 is a graph showing the comparison of oral versus IP administration of TER199 on bone marrow GM-CFC.

FIG. 4 shows the effect of oral versus IP administration of TER199 on bone marrow GM-CFC in a single treatment. The data are mean ±SEM for three mice per group. The asterisk indicates that the value is statistically significant from the control, P<0.05. As shown in FIG. 4, IP administration (open squares □) is most effective at 60–90 mg/kg; oral administration (open circles ○) is most effective at 120–180 mg/kg. The results show that the compounds of the invention may be administered orally as well as IP, although higher dosage levels may be required for oral administration.

EXAMPLE 6

Figure 5:
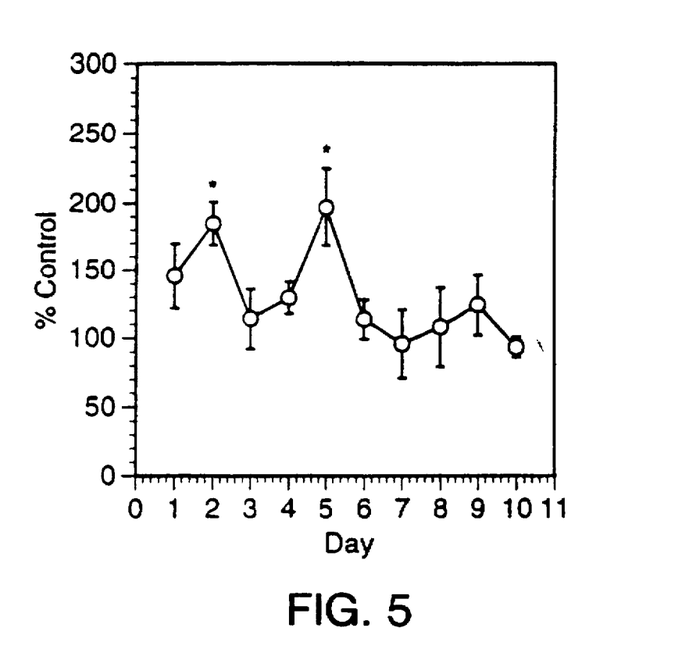
FIG. 5 shows the time course of TER199 stimulation of GM-CFC administered IP.

Time Course of TER199 Stimulation of Bone Marrow Macrophage (GM) Progenitors The procedures of Example 5 were repeated using a single dose of TER199 6 mg/kg administered IP on day 0 and harvesting bone marrow cells at various times after administration. The GM-CFC for the mice administered TER199 was compared to controls, and the results are shown as a function of day after administration in FIG. 5. Maximum stimulation appeared to occur at day 2 and day 5.

EXAMPLE 7

TER199 Amelioration of the Effect of Chemotherapeutic Agents

The male B62F$_1$ mice described in Example 5 were administered 75 mg/kg of five fluorouracil (5-FU) prepared in 0.9% sterile saline and administered IP. The bone marrow cells of the mice were harvested 24 hours after administration and GM-CFC was determined to be 20–30% of control mice.

Mice in groups of three were injected IP with 60 mg/kg TER199 in sterile water either simultaneously with 5-FU administration or 1–24 hours prior to 5-FU administration. The control group was not treated with either drug. When TER199 was administered 1 or 24 hours prior to 5-FU, the GM-CFC was increased to approximately 40% of control; when given 2 hours prior to 5-FU, of GM-CFC was about 60% of control; however, none of these values were statistically significantly different from control.

In an additional experiment, TER199 was administered 24 hours subsequent to 5-FU administration and the bone marrow cells were harvested in assay 24 hours after TER199 was administered. A statistically significant recovery in GM-CFC was then observed; GM-CFC values were approximately 120% of control, a 5-fold increase compared to treatment with 5-FU alone. 5-FU treated mice assessed at the same time gave GM-CFC values only 30% of the control.

Figure 6A:
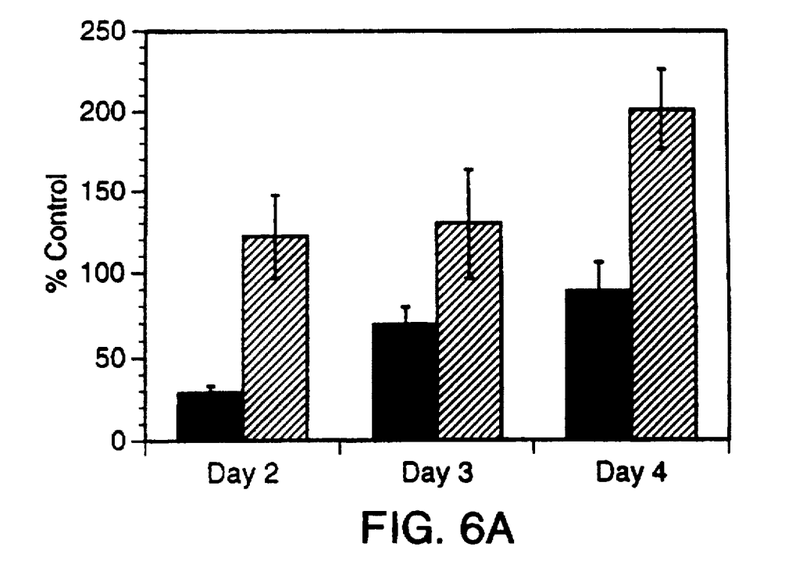
FIG. 6a is a graph showing the effect of administering TER199 24 hours after administration of 5-FU on the recovery of the differentiation ability of bone marrow cells.
Figure 6B:
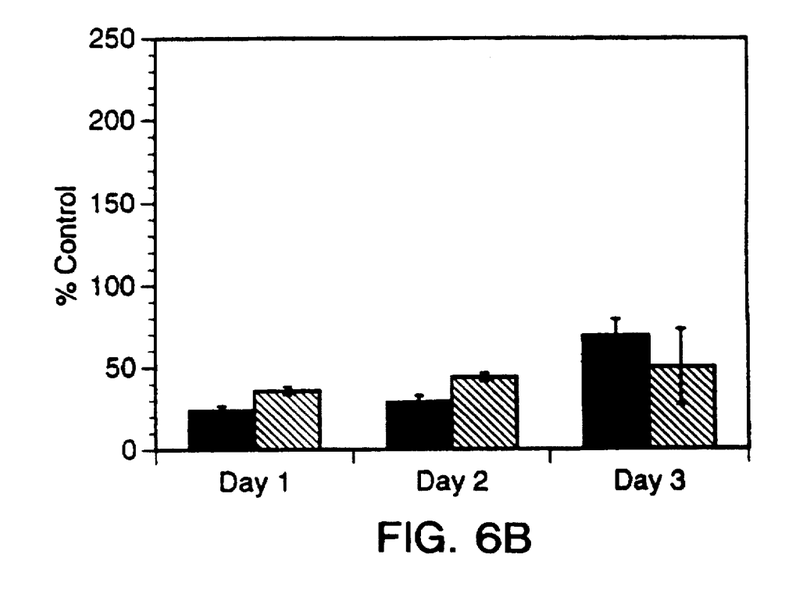
FIG. 6b is a similar representation of the results when TER199 is administered before administration of 5-FU.

Administration of TER199 as described above 24 hours after administration of 5-FU hastened the recovery of the differentiation ability of bone marrow cells and resulted ultimately in stimulation of this capability above controls not administered 5-FU. These results are summarized in FIG. 6a which shows that by day 4 after 5-FU administration, mice administered 5-FU only (closed bar, ■) showed GM-CFC approximately equal to control while those which had received TER199 in addition to 5-FU (hatched bar, ƒ) showed GM-CFC about twice that of control. Similar experiments but administering TER199 24 hours prior to 5-FU had essentially no effect on GM-CFC as shown in FIG. 6b.

The effects of TER199 administered 24 hours after injection of 5-FU by an IP route were also obtainable when the TER199 was administered orally. Bone marrow harvested 48 hours after administering 75 or 150 mg/kg 5-FU by IP showed levels of GM-CFC of <10% of control mice. However, GM-CFC levels were returned to normal 48 hours after 5-FU administration when 150 mg/kg TER199 was given by gavage 24 hours after 5-FU administration.

Substituting cisplatin for 5-FU as the chemotherapeutic agent showed TER199 was still protective with respect to GM-CFC levels although the timing pattern was different. Administering 15 mg/kg or 20 mg/kg cisplatin IP resulted in lowering the GM-CFC to 30% or 15% of control, respectively. A single oral dose of 150 mg/kg TER199 resulted in GM-CFC levels at 45% and 55% of control given 24 hours after or 24 hours before administering 20 mg/kg cisplatin, respectively. Bone marrow was harvested for these measurements 24 hours after cisplatin administration when TER199 was provided prior to cisplatin; bone marrow was harvested 48 hours after cisplatin administration when TER199 was given 24 hours after cisplatin. Thus, either prior or subsequent administration of TER199 orally reversed the destruction of bone marrow differentiation by cisplatin.

EXAMPLE 8

Structural Requirements

Figure 7:
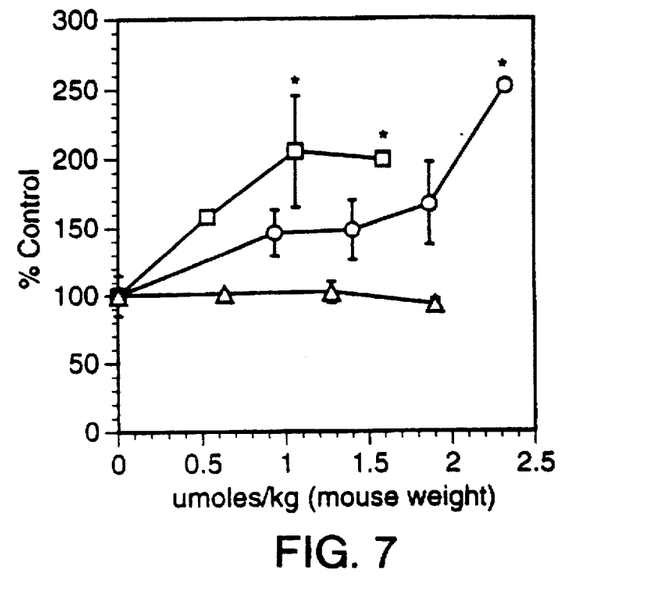
FIG. 7 shows the dependence of the esterified or amidated form of the tripeptides with respect to GM-CFC stimulation.

The effect on bone marrow differentiation by various derivatives and structural analogs of TER199 as a function of dosage level was also determined. Bone marrow was harvested 24 hours after administering the compounds and GM-CFC levels measured as described above. FIG. 7 shows that the diethyl ester is significantly more effective than the mixed ester amide in that the corresponding unesterified compound is not effective. In FIG. 7, the open triangles (Δ) represent the unesterified compound (TER117); the open circles (○) represent the mixed ester amide (TER300). The open squares (□) represent the results with the diethyl lester, TER199. The mixed ester amide, TER300 is known to be metabolized more slowly than TER199. Metabolism of TER300 produces TER117. The results in FIG. 7 are consistent with the inability of TER117 to enter the cells and the slower metabolism of TER300.

Figure 8:
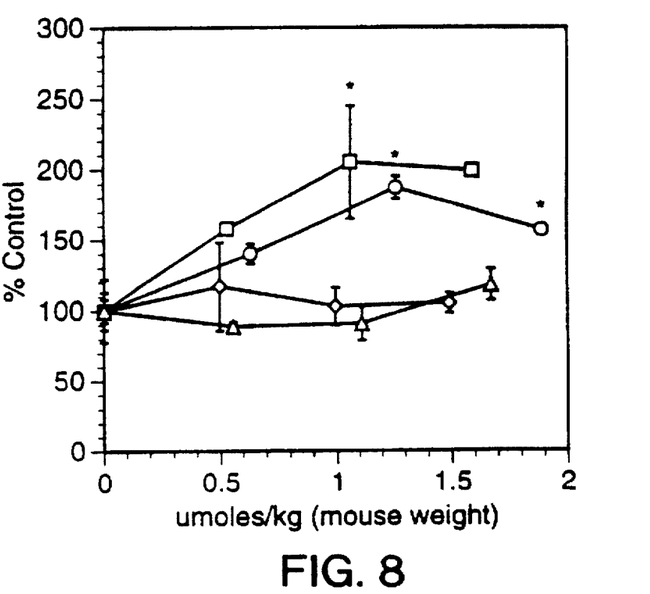
FIG. 8 shows the effect of the nature of the "X" substituent of Formula 1 on stimulation of GM-CFC.

FIG. 8 shows results of similar experiments for TER199 and its analogs. The open squares (□) represent TER199; open circles (○) represent TER183 where the benzyl group in TER199 is replaced by octyl and φG by G. The open diamonds (◇) and open triangles (Δ) represent the inactive compounds TER317 and TER206, respectively; in TER317, phenylglycine of TER199 is replaced by (S+)phenylalanine; in TER206 the benzyl of TER199 is replaced by naphthol and phenylglycine by glycine. These results correlate with the targeting of P1-1 GST isoenzyme by TER199 and TER183 as shown in Table 4, although TER183 is a better inhibitor of A1-1 than of P1-1.

TABLE 4

Structure, GST K$_i$ Values and bone marrow differentiation enhancement effect for glutathione analogs

| | | Ki (μM)* | | | | |
|---|---|---|---|---|---|---|
| TER | Structure | P1-1 | A1-1 | M1a-1a | M2-2 | BMDE** |
| 199 | γE-C(benzyl)-φG | 0.4 | 20 | 25 | 31 | + |
| 183 | γE-C(octyl)-G | 1.9 | .27 | 1.2 | n.d. | + |
| 317 | γE-C(benzyl)(S+)-φA | >10$^3$ | >10$^3$ | >10$^3$ | >10$^3$ | − |
| 206 | γE-C(naphthyl)-G | 1.2 | 4.2 | .01 | 1.5 | − |

*determined on unesterified form
**bone marrow differentiation enhancement

EXAMPLE 9

Stimulation of Cytokine Production

Human stromal cell cultures were established from freshly obtained human bone marrow as described by (Reference). On day 2, the cells were exposed for one hour to 100 μM TER199; culture medium was removed and replaced with fresh medium, and at 24 and 48 hours later, culture supernatants were collected and tested for the presence of interleukin-1 (IL-1). IL-1 levels were more than twice those of controls at both 24 and 48 hour time points.

EXAMPLE 10

Peripheral Blood Response to 5-FU Treatment+ TER199

Figure 9A:
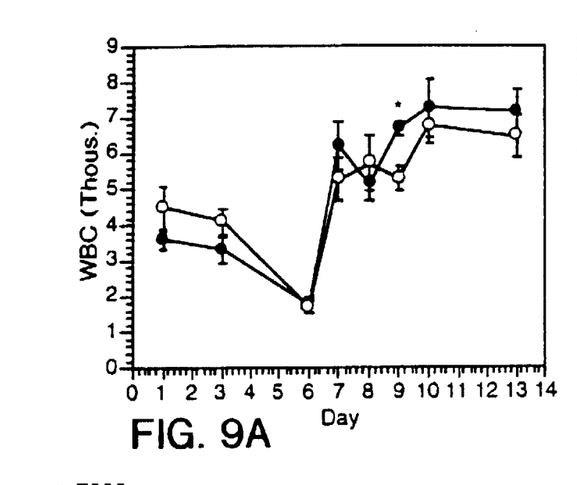
FIG. 9a–9d show blood counts of various types of cells after administering 5-FU alone or 5-FU+TER199.
Figure 9B:
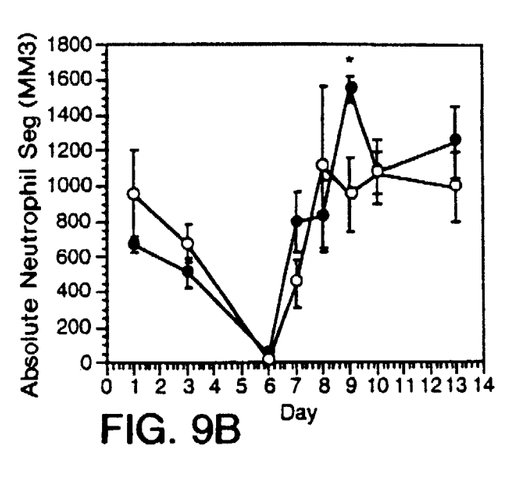
Figure 9C:
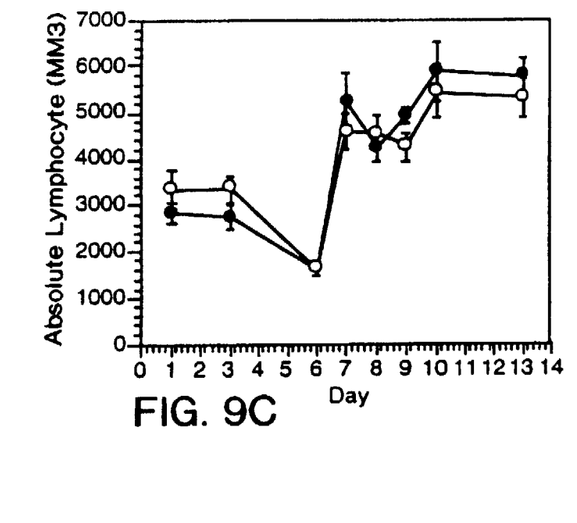
Figure 9D:
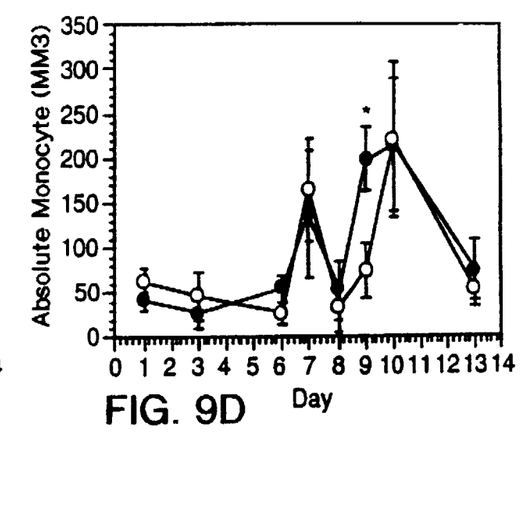

The treatment protocol of administering 150 mg/kg 5-FU IP followed 24 hours later by an oral dose of 150 mg/kg TER199 or vehicle in controls, followed 48 hours after 5-FU administration was repeated with additional groups of six mice each. The mice were bled through the retroorbital plexus and the blood samples were analyzed for changes in blood counts. The results in FIGS. 9a–9d show the blood counts of various types of cells for administering 5-FU alone (open circles, ○) or 5-FU plus TER199 (solid circles, ●). FIG. 9a shows the results for total white cell counts; essentially no significant difference was found. FIG. 9b shows the results for neutrophils; a statistically significant difference was obtained only on day 9. FIG. 9c shows the results for lymphocytes; no differences were found. FIG. 9d shows the results for monocytes; there was a statistically significant difference only on day 9.

We claim:

1. A method to stimulate the differentiation of bone marrow which method comprises contacting said bone marrow with a compound of the formula (1)

or the ester, amide, mixed ester/amide or salt forms thereof,
wherein YCO is γ-glu or β-asp;
G* is phenylglycine or glycine;
Z is CH$_2$, O or S; and
X is a hydrocarbon radical of optionally substituted on any aromatic moiety contained therein selected from the group consisting of hexyl, heptyl, octyl, benzyl and naphthyl;

in an amount and for a time effective to stimulate the differentiation of said bone marrow.

2. The method of claim 1 wherein Z is S.

3. The method of claim 1 wherein X is hexyl, heptyl, octyl, benzyl or naphthyl.

4. The method of claim 1 wherein X is benzyl or octyl.

5. The method of claim 1 wherein the compound of Formula 1 is in the diester form.

6. The method of claim 1 wherein the compound of Formula 1 is the diethyl ester of γ-glutamyl S-benzyl cysteinyl glycine, of γ-glutamyl S-octyl cysteinyl glycine, of γ-glutamyl S-benzyl cysteinyl phenylglycine, or of γ-glutamyl S-octyl cysteinyl phenylglycine.

7. The method of claim 1 wherein the compound of Formula 1 is the diethyl ester of γ-glutamyl S-benzyl cysteinyl phenylglycine or γ-glutamyl S-octyl cysteinyl glycine.

8. The method of claim 1 wherein said contacting is effected by administering said compound of Formula 1 or pharmaceutical composition thereof to a subject in need of said stimulation in an amount effective to stimulate the differentiation of the bone marrow progenitor cells.

9. The method of claim 7 wherein said subject is a human.

10. The method of claim 7 wherein said administering is intraperitoneal or intravenous or oral.

11. The method of claim 7 wherein the compound of formula (1) is the diethyl ester of γ-glutamyl S-benzyl cysteinyl phenylglycine.

12. The method of claim 11 wherein the γ-glutamyl and cysteinyl residues are in the native L form and wherein the phenylglycine residue is R(-) phenylglycine.

* * * * *